(12) United States Patent
Guo et al.

(10) Patent No.: US 10,640,505 B2
(45) Date of Patent: *May 5, 2020

(54) FOLATE DERIVATIVES, USEFUL IN PARTICULAR IN THE CONTEXT OF THE FOLATE ASSAY

(71) Applicant: BIOMERIEUX, Marcy-l'Etoile (FR)

(72) Inventors: Yuping Guo, Tassin la Demi-Lune (FR); Sylvie Cheucle, La Tour de Salvagny (FR)

(73) Assignee: BIOMÉRIEUX, Marcy-l'Etoile (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/897,713

(22) Filed: Feb. 15, 2018

(65) Prior Publication Data

US 2018/0170934 A1  Jun. 21, 2018

Related U.S. Application Data

(63) Continuation of application No. 14/655,258, filed as application No. PCT/FR2013/053271 on Dec. 27, 2013, now Pat. No. 9,926,323.

(30) Foreign Application Priority Data

Dec. 27, 2012  (FR) .................................... 12 62898

(51) Int. Cl.
*G01N 33/82* (2006.01)
*C07D 475/04* (2006.01)

(52) U.S. Cl.
CPC ............ *C07D 475/04* (2013.01); *G01N 33/82* (2013.01)

(58) Field of Classification Search
CPC combination set(s) only.
See application file for complete search history.

(56) References Cited

U.S. PATENT DOCUMENTS

| 4,337,339 A | 6/1982 | Farina et al. |
| 4,314,988 A | 9/1982 | Farina et al. |
| 4,418,151 A | 11/1983 | Forand et al. |
| 6,664,043 B2 | 12/2003 | Natrajan et al. |
| 9,926,323 B2 * | 3/2018 | Guo ....................... G01N 33/82 |

FOREIGN PATENT DOCUMENTS

| CN | 101092416 A | 12/2007 |
| EP | 0382334 A2 | 8/1990 |
| EP | 1273917 A2 | 1/2003 |
| FR | 2366291 | 9/1977 |
| FR | 2455602 A1 | 11/1980 |
| FR | 2781802 A1 | 2/2000 |
| WO | 80/00262 | 2/1980 |
| WO | 80/00562 A1 | 4/1980 |

(Continued)

OTHER PUBLICATIONS

Antony, "The Biological Chemistry of Folate Receptors," J. Amer. Soc. Hematol. (Jun. 1, 1992), 79(11):2807-2820.

(Continued)

*Primary Examiner* — Shafiqul Haq
(74) *Attorney, Agent, or Firm* — McDonnell Boehnen Hulbert & Berghoff LLP

(57) ABSTRACT

Use of a folate derivative to assay in vitro the folate in a sample such as a biological sample.

18 Claims, 3 Drawing Sheets

(56) References Cited

FOREIGN PATENT DOCUMENTS

| WO | 95/08000 A2 | 3/1995 |
| WO | 2002/085908 A1 | 10/2002 |

OTHER PUBLICATIONS

Arcot et al., "Folate: Methods of Analysis," Trends Food Science Tech. (2005), 16:253-266.

Dueker et al., Determination of Blood Folate Using Acid Extraction and Internally Standardized Gas Chromatography-Mass Spectrometry Decision, Anal. Biochem. (2000), 283:266-275.

Hansen et al., "A Competitive Enzyme-Linked Ligand Sorbent Assay (ELLSA) for Quantitation of Folates," Anal. Biochem. (1988), 172:160-164.

Owen et al., "Comparison of Five Automated Serum and Whole Blood Folate Assays," Am. J. Clin. Path. (2003), 120:121-126.

Pfeiffer et al., "Determination of Folate Vitamers in Human Serum by Stable-Isotope-Dilution Tandem Mass Spectrometry and Comparison with Radioassay and Microbiologic Assay," Clin. Chem. (2004), 50(2):423-432.

Reif et al., "Chromatographic Assays for Folic Acid," J. Pharma. Sci. (Aug. 1977), 66(8):1112-1116.

Waxman et al., "Determination of Folate by Use of Radioactive Folate and Binding Proteins," Meth. Enzymol. (1980), 66:468-483.

Wright et al., "Analogs of Pteroylglutamic Acit. IV. Replacement of Glutamic Acid by Other Amino Acids," J. Am. Chem. Soc. (Sep. 1, 1949) from http://pubs.acs.org/doi/pdf/10.1021/ja01177a019, p. 3015.

Huang et al., "Homogeneous Bioluminescence Competitive Binding Assay for Folate Based on a Coupled Glucose-6-phosphate Dehydrogenase-Bacterial Luciferase Enzyme System," Anal. Chem. (Jan. 1, 1996), 68(9);1646-1650.

Muller et al., "Organometallic <99m>Tc-technetium(I)- and Re-rhenium(I)-folate Derivatives for Potential Use in Nuclear Medicine" Dec. 6, 2004, J. Organometallic Chem. 689(25):4712-4721.

"Abbott Axsym System" from http://www.ilexmedical.com/files/pdf/folate_AXS.pdf retrieved Oct. 15, 2013.

International Search Report of PCT/FR2013/053271 dated Mar. 24, 2014.

Examination Report in related application CN201380073802.9, dated Mar. 2, 2016 (with English summary).

\* cited by examiner

Figure 2:
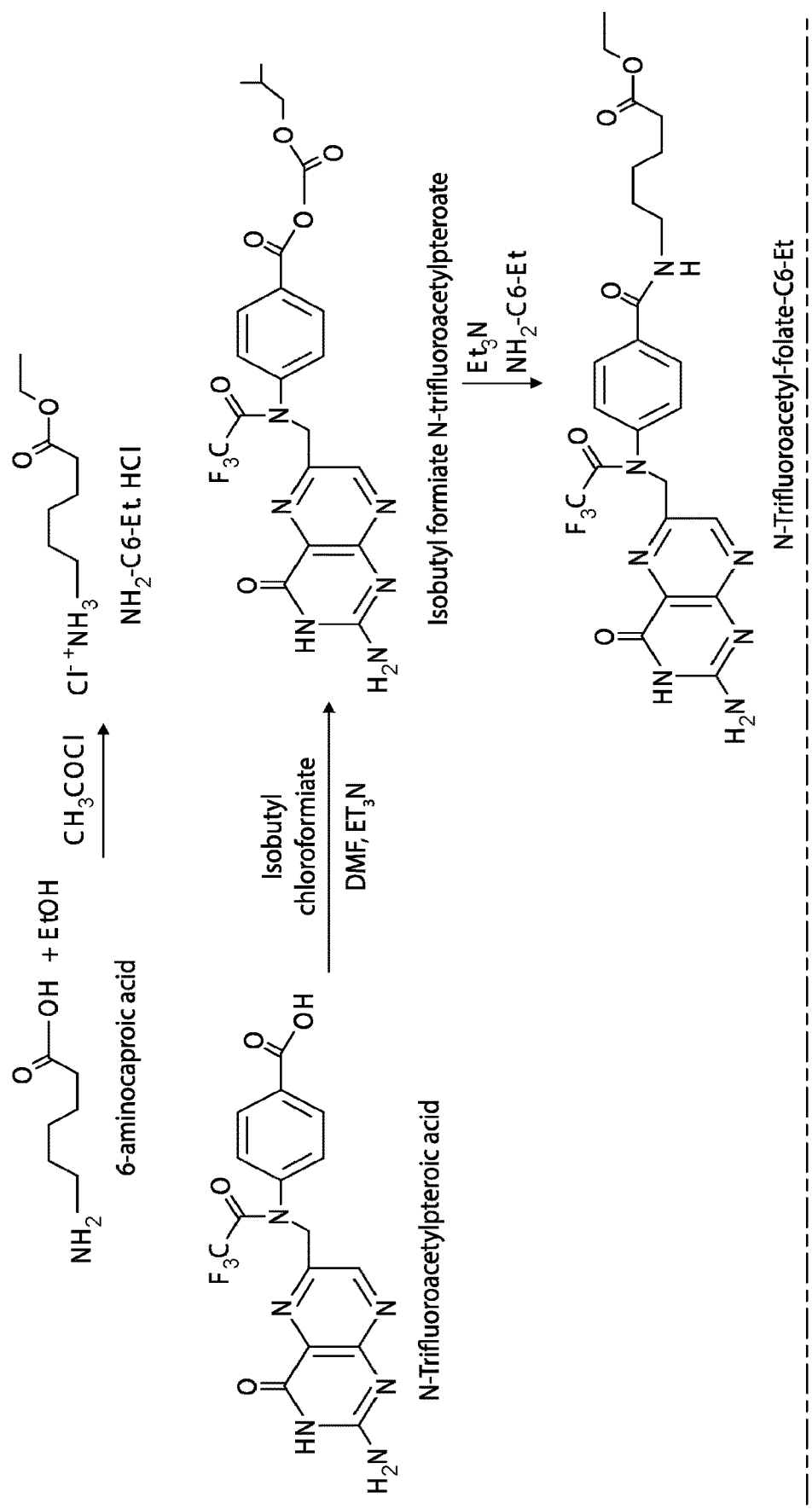

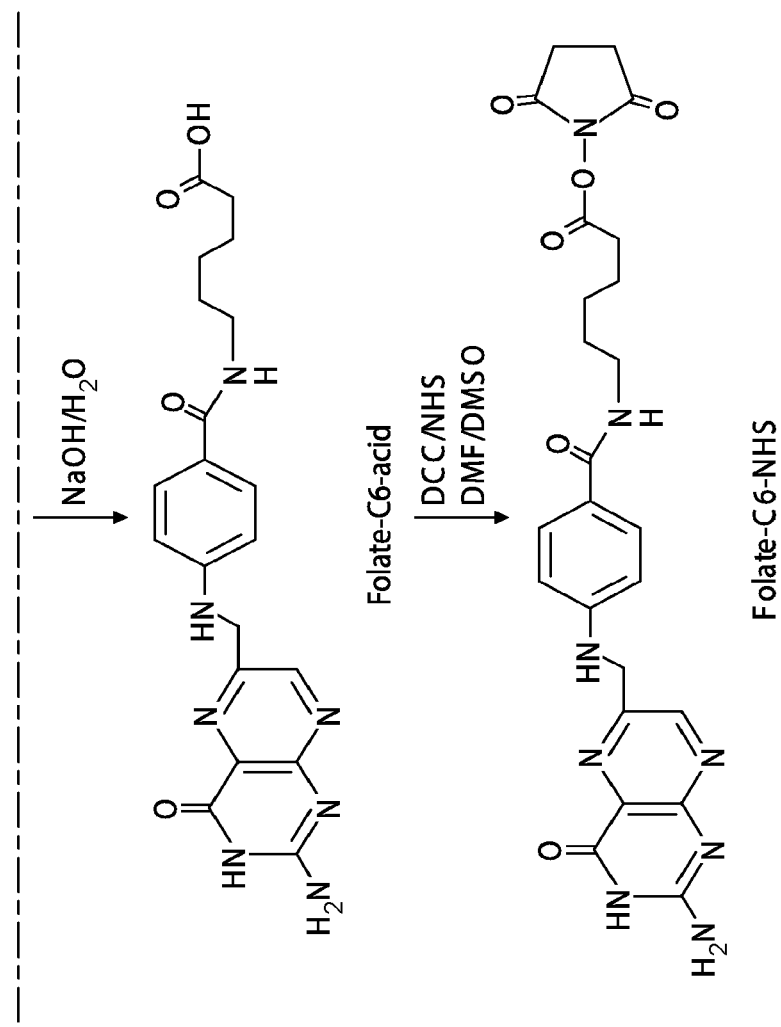
Figure 2 Continuation

FOLATE DERIVATIVES, USEFUL IN PARTICULAR IN THE CONTEXT OF THE FOLATE ASSAY

CROSS-REFERENCE TO RELATED APPLICATIONS

This application is a Continuation of U.S. Nonprovisional patent application Ser. No. 14/655,258 entitled "FOLATE DERIVATIVES, USEFUL IN PARTICULAR IN THE CONTEXT OF THE FOLATE ASSAY," filed Jun. 24, 2015, which is a U.S. national stage filing under 35 U.S.C. § 371 of International Application No. PCT/FR2013/053271 entitled "FOLATE DERIVATIVES, USEFUL IN PARTICULAR IN THE CONTEXT OF THE FOLATE ASSAY," filed on Dec. 27, 2013, which claims priority from French Patent Application Serial No. 1262898, filed Dec. 27, 2012. The contents of each of these applications are incorporated herein by reference in their entireties.

TECHNICAL FIELD

The present invention relates to folate derivatives, particularly useful for assaying a folate/folate(s) in an in vitro biological sample, preferably employing non-radioisotopic competition techniques.

STATE OF THE ART

Vitamin B9 is the generic denomination given to a very chemically and biologically closely related family of compounds, all derived from folic acid. One of the main characteristics of these compounds is that their presence in insufficient quantity, or their actual absence, causes anaemia in man or in an animal. The folates family comprises, inter alia, vitamin M, vitamin Bc, folacin and folic acid. Within the meaning of the present application, each of the compounds belonging to this family is called "folate", a plurality of members of this family is called "folates", while the mixture of constituents of the vitamin B9 family of is called "total folate".

As is well-known to the man skilled in the art, folic acid, also called pteroylmonoglutamic acid, is formed of a pterin group, a p-aminobenzoic group and a glutamate group as represented hereinafter by general formula (G):

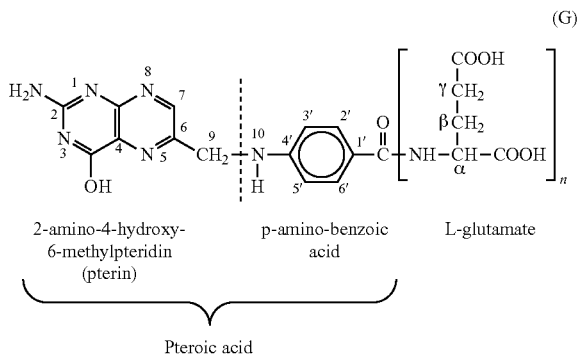

in which n is the integer 1.

As shown in this general formula, folic acid has two carboxylic acid functions on its glutamate part, one in the a carboxylic position, the other in the γ position.

In food, folates are mostly in the form of reduced methyl- or formyl-polyglutamates. On digestion, these polyglutamates are transformed into monoglutamates, actively absorbed by the enterocytes. Then, the monoglutamates are transformed into 5-methyltetrahydrofolate (5-MTHF), in which form the folates pass through the intestinal barrier and pass into the systemic circulation.

In blood, the major part of the circulating folates is bound with a weak affinity to various proteins: α2-macroglobulin (40%), albumin (33%) and transferrin (23%). Plasma concentrations of vitamin B9 vary from 5 to 15 µg/L and are heavily impacted by food intake. The vitamin B9 concentration is approximately 20 times higher in the red blood corpuscles which can contain up to 95% of the circulating folates. Multiple forms of folates are present in human serum, but the preponderant circulating and intracellular form is 5-methyltetrahydrofolate (5-MTHF), which is also the form of hepatic storage. Generally, the biologically active compounds are solely the reduced forms: dihydrofolate (DHF), and mainly tetrahydrofolate (THF) as well as its methyl or formyl derivatives. As indicated above, within the meaning of the present application, the denomination "folates" covers in particular these reduced forms; each of said forms, taken separately, being called "folate".

Eucaryotic cells, as well as certain procaryotic cells, are incapable of synthesising folic acid. They therefore use transmembrane transport systems which allow internalisation of the exogenous molecule. At the present time, two main transport systems have been described. However, there probably also exist secondary routes such as passive diffusion. Oxidised folates like folic acid are transported inside cells by the folate receptors (FR), "folate receptors" in the English language (Antony, 1992 [1]). These proteins were formerly called "folate binding proteins" (FBPs). Three isoforms have been identified in man, respectively called FRα (P15328), FRβ (P14207) and FRγ (P41439), the code indicated between parentheses corresponding to the identifier of the protein in the UniProt database (http://www.uniprot.org). FRα and β are anchored in the plasmatic membrane by a lipid part, glycosylphosphatidylinositol (GPI). The γ isoform is secreted. The reduced folates, for their part, are transported by a protein called reduced folate carrier (P41440) or "reduced folate carrier" in the English language (RFC). This is a highly glycosylated integral membrane protein which has a plurality of transmembrane domains.

Due to their chemical structure, folates play an essential role in the synthesis and metabolism of the basic constituents of our organism, namely amino acids and bases (purines and pyrimidines).

THF, an essential coenzyme, is capable of fixing and transferring radicals to a carbon atom. It is involved in the synthesis of glycine and the catabolism of histidine.

5-MTHF permits remethylation of homocysteine to methionine via methylcobalamin and methionine synthase. Folates are also involved in several key steps of the biosyntheses of purines and pyrimidines, thus affecting the synthesis of the nucleic acids DNA and RNA. Because of this central role, folate(s) deficiency has serious consequences and many physiopathological expressions.

Severe folate deficiency gives rise to general, haematological and neuropsychiatric signs. Slowly, asthenia and anorexia appear. Anaemia can be preceded by isolated macrocytosis. This anaemia, often of megaloblastic type, is one of the most frequent expressions of folates deficiency. In addition there is often a combined deficiency of folates and of iron which results, instead of classic macrocytic anaemia, in normocytic anaemia with presence of Jolly bodies on the smear. This anaemia is due to the fact that purines and pyrimidines are not available in sufficient quantity, thus resulting in the impossibility of blood stem cells synthesising genetic material and therefore dividing. Conversely, the existing cells continue to grow, which partially explains the generally megaloblastic type of the anaemia associated with folate deficiency.

Folates are also necessary for proper functioning of the brain, and contribute to mental health and emotional balance. Thus, vitamin B9 deficiency causes neuropsychiatric problems. These problems could in part be linked to anomalies in the synthesis of certain amines and glycine. The latter is also a neurotransmitter.

Due to their contribution to the synthesis of genetic material, a satisfactory intake of folates is particularly necessary during childhood, adolescence and pregnancy. Indeed, psychomotor retardation and staturo-ponderal hypotrophy are often found in children having folates deficiencies. During pregnancy, a folate(s) deficiency can cause delay or anomalies in the development of the foetus, or even congenital deformities such as spina bifida which is incomplete closure of the neural tube, or even trisomy.

Folates deficiency is also associated with increased risk of cardiovascular illnesses, more precisely arterial and/or venous thromboses and atheroscleroses. The risk is linked to the increase in the plasmatic homocysteine level, resulting from lack of methylation of this compound into methionine.

This list is not limiting and folates deficiency can cause other disorders/pathologies. It is therefore of primary importance to be able to assay all or part of the folates in a human or animal individual, preferably the "total" folate, i.e. formed by the mixture of the different folate forms.

In addition, it is also important to be able to quantify all or part of the folates present in samples of food origin (intended for human or animal consumption) in order to verify the vitamin B9 contribution of the foods in question. It may also prove advantageous to assay the folates in products of food type, in order to ensure that these contain a sufficient quantity/concentration of folate(s). Such food supplements can in particular serve to prevent possible vitamin B9 deficiencies.

Assaying the folates in whole blood, serum, plasma, or in the red blood cells has a certain advantage from a clinical point of view. Reduction in the blood folates concentration potentially results inexpresses a deficiency which should be clinically investigated, possibly in association with other vitamin or metabolite assays. The blood folates level is subject to variations depending on diet or the taking of medications. It is the folates level of red blood cells which gives the best estimate of the folates reserves of the organism.

Several methods exist to permit the quantification of plasma, serum and/or red blood cell folates in biological samples of clinical origin, i.e. coming from patients. These methods can be classified in three main groups, i.e.: (1) microbiological techniques, (2) chromatographic techniques and (3) competition immunoassays.

Microbiological techniques (1) generally use a "folates-dependent" seed, the growth of which is proportional to the vitamin level present in the sample to be assayed. Generally, the samples are deproteinised at 100° C. in the presence of vitamin C, which acts as an antioxidant. Contact with the bacterial strain is effected for 20 hours at 37° C. The seed germ most frequently used, *Lactobacillus casei*, is sensitive to all the oxidised and reduced forms of folates; other seeds are sensitive to more specific forms. For example, *Streptococcus faecalis* permits the assay of all forms of folates with the exception of 5-MTHF. The concentration of 5-MTHF, the preponderant form in serum and red blood cells, is obtained by the difference between the values of *L. casei* and of *S. faecalis*. A third seed, *Pediococcus cerevisiae*, is sensitive exclusively to N5-formyl-THF (folinic acid).

These microbiological techniques (1), though generally sensitive and reproducible, are tedious and time-consuming. In addition, they present risks of interference with antibiotics and antimitotics, such as methotrexate, trimethoprim and pyrimethamine.

Assays of chromatographic type (2) allow the separation of the different compounds belonging to the folates family. As examples of chromatographic assay, can in particular be cited:

thin-layer chromatography assay coupled with HPLC (Reif, V. D. et al., 1977 [2]), chromatography assay (generally gas or liquid phase) coupled with mass spectrometry (MS), for example by:
a) gas phase chromatography/mass spectrometry with isotope dilution (ID-GCMS) (Dueker, S. R. et al., 2000 [3]), or
b) liquid phase chromatography-mass spectrometry in tandem with isotope dilution (ID-LC-MS/MS) (Pfeiffer, C. M. et al., 2004 [4]).

These assays of chromatographic type (2) notably have the disadvantage of requiring the development of very technical tests, requiring qualified personnel. In addition, the instrument proves to be expensive.

Having regard to the problems encountered on implementation of the microbiological (1) and chromatographic (2) techniques (cf. above), competition immunoassays (3) have been developed. While reducing the analysis time, these latter (3) permit the assay of "total" folate and therefore the provision of a reliable clinical diagnosis relative to a possible folates deficiency.

These immunoassay processes (3), also called immunological assays or immuno-chemical tests, involve the binding of the analyte to be detected—in this case the folate (s)—with at least a first compound which is a binding partner to this analyte. As the folate(s) assay is effected by competition, the process also involves at least a second compound which enters into competition with the folate to be assayed in relation to fixing on the binding partner, this second compound being a folate derivative. The monitoring of this reaction involves labelling one of the two compounds. This labelled compound is called labelled conjugate or tracer.

Of course, the prefix "immuno", for example in "immunoassay", is not to be considered in the present application as strictly indicating that the binding partner is an immunological partner, such as an antibody or an antibody fragment. Indeed, as is well-known to the man skilled in the art, this term is more widely used to designate tests and processes in which the binding partner, also called ligand, is not an immunological partner but consists, for example, of a receptor of the analyte which is required to be assayed. The condition being that the binding partner is capable of binding to the analyte, preferably in specific manner. Thus, it is known to use the term ELISA (Enzyme-Linked Immunosorbent Assay) for assays which use non-immunological binding partners stricto sensu, more widely called in English "Ligand Binding Assay", which could be translated into French as "Dosage utilisant la liaison à un ligand", while the term "immuno" is included in the acronym ELISA. For the sake of clarity and uniformity, the term "immuno" is used in the present application to designate any assay using a suitable binding partner to bind to the analyte to be quantified, preferably in specific manner, even when this binding partner is not of an immunological nature or origin in the strictest sense.

In the context of competition immunoassays (3), and when a labelled conjugate is used, three types of competition immunoassays are distinguished depending on the nature of the labelled conjugate and on the type of signal emitted by said conjugate, i.e.:

- radio-isotopic immunoassays (Waxman S. and Schreiber C., 1980 [5]),
- immuno-enzymatic assays or EIA "enzyme-linked immunoassay-assay"; depending on the selected enzyme substrate, the signal can be of colorimetric type (Hansen, S. I. and Holm J., 1988 [6]) of fluorescence or chemiluminescent type,
- electrochemiluminescent immunoassays (Owen, W. E. and Roberts W. L. 2003 [7]).

The last two types of competition immunoassay are called "non-radioisotopic competition immunoassays".

The development of the radioisotopic methods (RIA), from the 1960s, revolutionised the quantification of vitamins and in particular of vitamin B9.

Patent application WO 80/00562 illustrates this by disclosing radioactive folate derivatives, substituted at the carboxylic acid function carried by the α carbon and/or by the γ carbon of the glutamate derivative. Radioactive labelling comes from the insertion of iodine-125 or 130 in the phenol ring of a tyrosine structure.

French patent application FR-A-2455602 also relates to obtaining radioiodinated compounds and mentions pteroic acid derivatives of general formula:

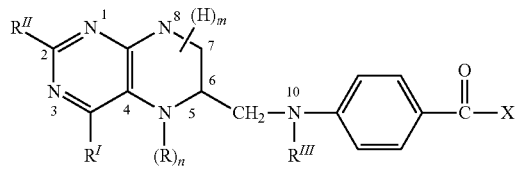

in which the glutamate group is replaced by the radical X, this radical X representing, as required, the residue of an amino acid or of a "des-carboxyamino acid" necessarily containing an aromatic or heterocyclic ring, indispensable for radioisotopic labelling (with iodine 125, 131 or 123). This iodinated aromatic or heterocyclic ring is separated from the p-aminobenzoic acid group by a chain not including more than 5 carbon atoms, attached to the p-aminobenzoic group by a secondary amine. As "des-carboxyamino acid residue" containing an aromatic or heterocyclic ring, the following structures are disclosed:

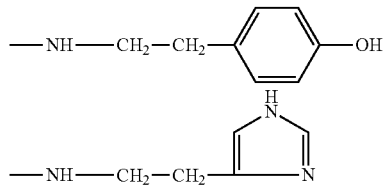

However, these radioisotopic assays (RIA) had in particular the disadvantage of the treatment of radioactive waste and the relatively short duration of the half-life of the labelled reagents.

This is why non-radioisotopic competition immunoassays have been developed to the detriment of RIA which is only rarely used today.

By way of illustration, the publication Arcot J. et al, 2005 [8] describes a process for assaying folic acid by binding to a protein tagged with an enzyme ("enzyme-labelled protein binding assay" in the English language), said labelled protein being FBP, and the process method being based on competition between the molecules of folic acid free in the biological sample and those previously immobilised on a microtitration plate to fix on the labelled FBPs. After rinsing, the revelation step is performed by introducing a colourless enzyme substrate, causing blue colouration after cleaving by the enzyme fixed to the FBP. As is generally the case in competition assays, the quantity of free folic acid present in the sample is determined by reference to a calibration curve, from which the quantity of free folic acid present in the sample is deduced as a function of the measured luminous intensity.

The Abbott Axsym Folate kit (Cat. No. B7K460, Abbott Laboratories) also permits the implementation of a competition folates assay process. As a binding partner, this kit uses the protein FBP and, as the labelled conjugate, pteroic acid (a folate analogue) bonded to alkaline phosphatase (ALPA). The principle of the test is based on competition between the folic acid to be assayed and the above-mentioned conjugate in the context of fixing to the soluble FBP. Following the competition reaction, the FBP is brought into contact with anti-FBP monoclonal antibodies and the antigen-antibody reaction takes place. Said antibodies are bonded covalently to carboxymethylamylose, a polyanion. Thus, the complexes are captured by polyanion-polycation electrostatic interactions, on a positively charged matrix. However, the Applicant has discovered that the sensitivity of this assay was not completely satisfactory, in particular regarding the quantification of low folates concentrations.

There is therefore an urgent need to improve the analytic sensitivity of non-radioisotopic folate immunoassays in order to obtain a process usable in samples of clinical origin (biological samples) and/or in samples of agri-food origin containing a low folate concentration.

STATEMENT OF THE INVENTION

The Applicant has, against all expectation, discovered novel folate derivatives which allow all or part of the disadvantages mentioned above to be remedied, in that their use in a non-radioisotopic competition assay (such as an immunoassay), in particular as tracer, allows an increased analytic sensitivity to be obtained, in particular in the ranges of lowest folate concentration.

Thus, an object of the invention relates to the use of a folate derivative for assaying folate(s) in vitro in a sample, such as a biological sample, said assay being a non-radioisotopic competition immunoassay and said folate derivative being decarboxylated in the α position. Said a position is such as shown in the general formula (G) mentioned above.

Indeed, the Applicant has in particular discovered, in surprising manner, that the folate derivatives decarboxylated in the α position significantly improved the analytic sensitivity of non-radioisotopic competition immunoassays allowing the in vitro assay of folate(s).

Preferably, the folate derivative according to the invention is different from the NSP-DMAE-HD-pteroate and NSP-DMAE-HEG-pteroate compounds represented respectively by formulae (A) and (B) in claim 1.

Advantageously, the folate derivative according to the invention does not comprise an —(O—CH$_2$—CH$_2$)— structure and is different from the NSP-DMAE-HD-pteroate compound represented by formula (A) in claim 1.

As indicated above, the prefix "immuno", for example in the term "immunoassay", must not be narrowly interpreted as designating a binding partner of immunological nature and/or origin, such as an antibody. Indeed, the binding partner used in the competition immunological test can be, for example, a receptor of the analyte which is required to be assayed, in this case the folates receptor. The non-radioisotopic immunoassay techniques applicable according to the present invention can be any techniques known to the man skilled in the art employing a binding partner binding with a sufficient affinity to the folate(s) for the competition assay to be correctly performed.

According to a preferred embodiment, the folate derivative according to the invention is used to assay a plurality of folates, or even, preferably, the total folate (as defined above).

According to a particular embodiment, the folate derivative according to the invention is used to assay folic acid (pteroylmonoglutamic acid).

The terms "to assay" and "assaying" relate, in the present application, to the determination of a quantity/concentration of the analyte(s) in question, i.e. of the folate(s).

The invention also has as its object the use of a folate derivative to assay the folate in vitro in a sample such as a biological sample, said assay being a competition immunoassay, preferably non-radioisotopic, said folate derivative responding to general formula (I):

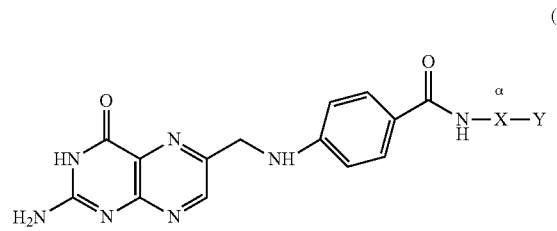

in which:
   X is an aliphatic hydrocarbon chain comprising 1 to 10 carbon atoms in which the carbon placed in the α position does not carry an acyl function such as a carboxylic acid function;
   Y represents a functional group suitable to allow bonding to a separate molecule M, such as a protein, said bonding comprising the formation of at least one covalent bond between Y and a functional group carried by said separate molecule M.

The invention also has as its object the use of a folate derivative to assay the folate in vitro in a sample such as a biological sample, said assay being a competition immunoassay, preferably non-radioisotopic, said folate derivative responding to general formula (I):

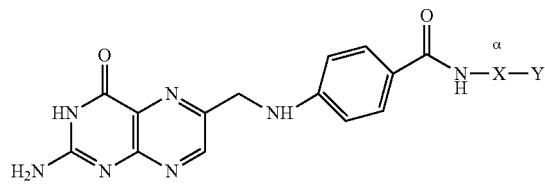

in which:
   X is an aliphatic hydrocarbon chain containing from 1 to 10 carbon atoms;
   Y represents a functional group suitable to allow bonding to a separate molecule M, such as a protein, said bonding comprising the formation of at least one covalent bond between Y and a functional group carried by said separate molecule M.

By "aliphatic hydrocarbon chain" is understood, within the meaning of the present invention, a linear or open branched (acyclic) hydrocarbon chain. According to the definition commonly accepted and presented in the reference works, a hydrocarbon chain must quite obviously be understood, within the meaning of the present invention, as only containing hydrogen (H) and carbon (C). In other words the aliphatic hydrocarbon chain X is solely functionalised by the functional group Y mentioned above and, by definition, does not contain a heteroatom (such as oxygen, nitrogen, sulphur, phosphorus, halogens, etc.).

The combination of deacylation (of which decarboxylation is an example) in the α position of the folate derivative according to the invention and of an aliphatic hydrocarbon chain comprising from 1 to 10 carbon atoms results in folate derivatives giving excellent analytic sensitivity when they are used in competition immunoassays (preferably non-radioisotopic).

Said molecule M is, for example, a labelling molecule Mm. This molecule M can also consist of a chemical arm or "linker".

Preferably, X is a hydrocarbon chain comprising from 2 to 7 carbon atoms, preferably from 3 to 5 carbon atoms, advantageously X is a hydrocarbon chain of 3 carbon atoms or 5 carbon atoms.

Advantageously, X is a saturated hydrocarbon chain.

Preferably, X is a linear hydrocarbon chain.

According to a particularly preferred embodiment, X is a linear and saturated aliphatic hydrocarbon chain, comprising a number of carbon atoms as defined above. In other words, and according to this particularly preferred embodiment, the folate derivative according to the invention can be represented by the following general formula (I'):

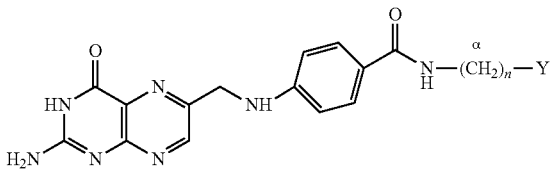

in which:
n is an integer between 1 and 10. Advantageously, n is an integer between 2 and 7, preferably between 3 and 5, advantageously n represents the integer 3 or 5.
Y is as defined above.

According to a preferred embodiment, Y is is a group of electrophilic centre type or a group of nucleophilic centre type, preferably a group of electrophilic centre type, suitable to allow the formation of an amide, ester, or thioester bond, preferably amide or ester, advantageously amide, between Y and the functional group carried by said separate molecule.

According to a preferred embodiment, Y is a group of electrophilic centre type, responding to the following general formula (II):

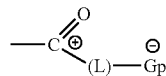

(II)

in which Gp is a leaving group, optionally bonded to the carbonyl function by an L arm, Gp being suitable to be dissociated from the group of electrophilic centre type in a reaction with a nucleophilic group carried by said separate molecule M, such as a primary amine.

The presence of the L arm is therefore optional in the compound of general formula (II), for which reason this L arm is shown between parentheses in said formula. Thus, for the purposes of the present application, the group of formula (L)-Gp can therefore designate a group of formula L-Gp (presence of the L arm) or a leaving group Gp (absence of said L arm).

Preferably, said reaction of the group of electrophilic centre type of general formula (II) with said nucleophilic group carried by said molecule M—such as a primary amine—is a nucleophilic substitution reaction.

Still in the preferred embodiment according to which Y is a group of electrophilic centre type, the (L)-Gp group is selected from groups suitable to allow the formation of an amide, ester, or thioester bond, preferably amide or ester, advantageously amide, between said group of electrophilic centre type and a functional group carried by said separate molecule M. Preferably, the latter is a nucleophilic group such as a primary amine.

Advantageously, the (L)-Gp group is selected from: —OH, —NH—$(CH_2)_m$—COOH, —$N_3$,

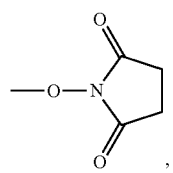

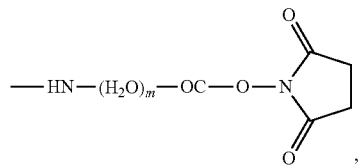

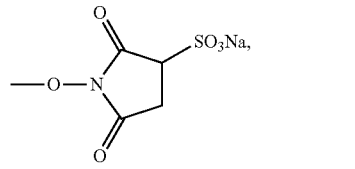

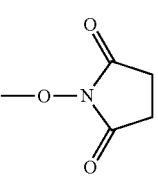

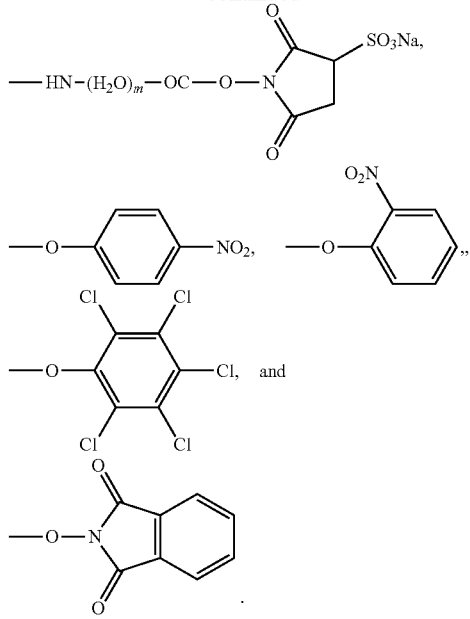

$m$ being an integer between 1 and 10.

Among the above-mentioned (L)-Gp groups, the man skilled in the art will be able to distinguish, without excessive difficulty, the Gp leaving groups (such as the groups —OH, —$N_3$ and —N-oxy-succinimide) from the L-Gp groups, i.e. in particular:

—NH—$(CH_2)_m$—COOH,

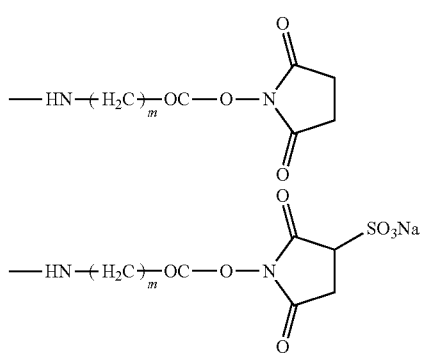

in which the L arm is formed by the —NH—$(CH_2)_m$—CO (or —NH—$(CH_2)_m$—OC) part.

For the sake of clarity, it will be noted that the group called above "—N-oxy-succinimide" is the group of the following formula:

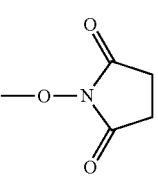

The use of such (L)-Gp groups favours the formation of an amide, ester, or thioester bond, preferably amide or ester, advantageously amide, between the group of electrophilic centre type Y and a functional group carried by the separate molecule M. These (L)-Gp groups are particularly suitable to allow the formation of an amide bond between said group of electrophilic centre type and an amine function—such as a primary amine—carried by the molecule M.

Preferably, m is between 1 and 5, advantageously between 1 and 3.

Advantageously, Y is a group of electrophilic centre type of general formula (II) and the (L)-Gp group is selected from:

—OH and —NH—$(CH_2)_m$—COOH and

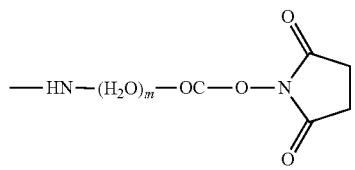

m being between 1 and 10 and preferably m being equal to 1.

According to a particularly preferred embodiment, Y is a group of electrophilic centre type of general formula (II) and (L)-Gp is the L-Gp group of the following formula:

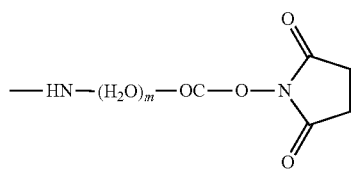

In other words, the folate derivatives of the invention are therefore characterised by general formula (I) such as given above, in which X is as defined above and Y represents a bonding group activated or ready to be activated to allow the formation of an amide, ester or thioester bond, preferably amide or ester, advantageously amide, between said derivative and a functional group carried by said separate molecule M.

According to a particularly preferred embodiment, Y is a bonding group activated or ready to be activated to allow the formation of an amide bond with a primary amine of said molecule M. In this embodiment, the molecules which can be bonded to the folate derivatives of the invention are all molecules which naturally have a primary amine, such as a protein, or any molecules which have been chemically modified to include such a primary amine, for example a modified biotin, having a primary amine.

By "bonding group activated or ready to be activated", is understood a functional group suitable, where necessary after activation, to allow the bonding of the folate derivatives of the invention to a functional group carried by said separate molecule M (for example to a primary amine carried by the latter).

According to a particularly preferred embodiment, Y is an activated bonding group which allows the direct formation of an amide bond with a functional group carried by the molecule M (for example a primary amine), without this group needing to be previously modified. By way of example, the following groups can be cited:

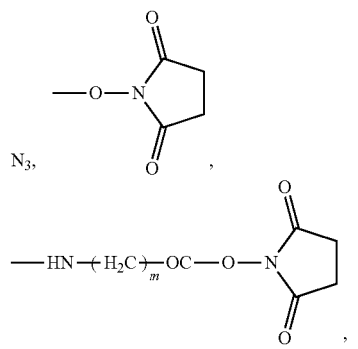

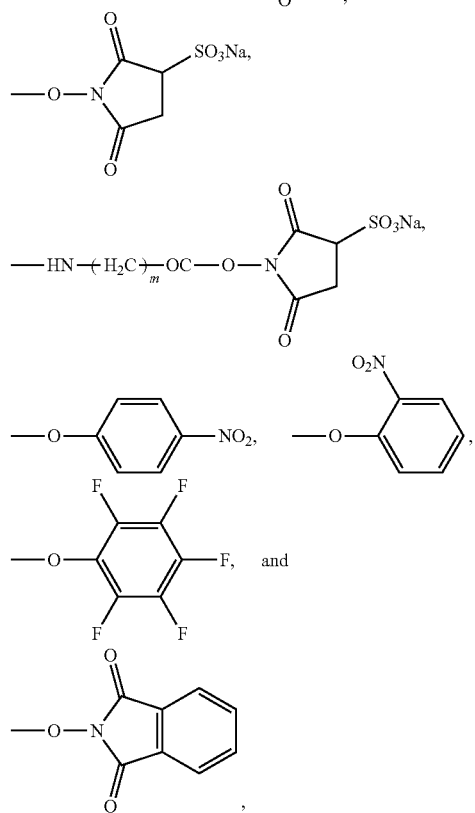

m being an integer, preferably between 1 and 10, which constitutes an embodiment of the invention.

According to an alternative embodiment of the present invention, Y is a bonding group ready to be activated, i.e. any group which must be activated, by methods known to the man skilled in the art, to be capable of forming an amide, ester or thioester bond, preferably amide or ester, advantageously amide.

According to a particularly preferred embodiment, Y is a bonding group ready to be activated to form an amide bond between the folate derivative according to the invention and said molecule M. Such groups have an —OH or —COOH group. As examples can be cited the groups —OH and —NH—$(CH_2)_m$—COOH; m being an integer, preferably between 1 and 10, which constitutes an embodiment of the invention.

According to a particular embodiment of the invention, m is between 1 and 5, or between 1 and 3.

According to another embodiment, Y is selected from —OH, —NH—$(CH_2)_m$—COOH, and

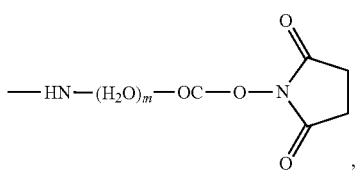

m being between 1 and 10 and preferably being equal to 1.

According to another particularly preferred embodiment, the derivative of general formula (I) is used in conjugate form with said molecule M, and said conjugate being represented by the following general formula (III):

(III)

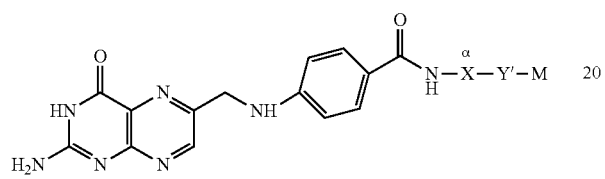

in which X and M are as defined above, and in which Y' is a derivative of the functional group Y after bonding of the derivative of general formula (I) to said molecule M, said molecule M preferably being a labelling molecule Mm.

This conjugate of general formula (III) is different from the compound NSP-TMAE-HD-pteroate represented by formula (A) in claim 1.

Preferably, Y' is represented by the following general formula (IV):

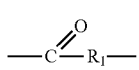

(IV)

or by the following general formula (V):

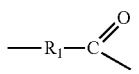

(V)

wherein R1 is —NH—, —O—, or —S—, preferably —NH— or —O—, advantageously —NH—;

Y' being preferably represented by general formula (IV).

When Y' corresponds to general formula (IV), the conjugate according to the invention can be represented by the following general formula (III'):

(III')

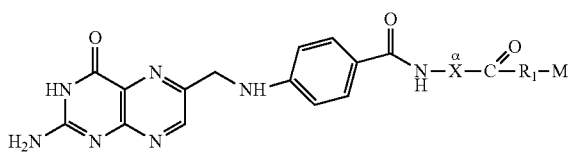

in which X, $R_1$ and M are as defined above.

According to a particularly preferred embodiment, $R_1$ is —NH— and formula (III') is as follows:

(III')

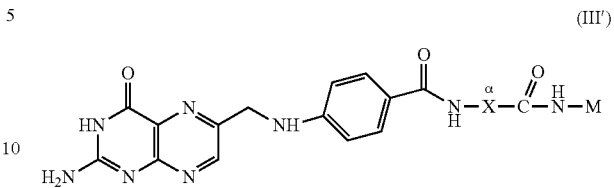

in which X and M are as defined above.

According to a particularly preferred embodiment, still when Y' is a group of general formula (IV), X is —$(CH_2)_n$— and the conjugate according to the invention is represented by the following general formula (III'):

(III')

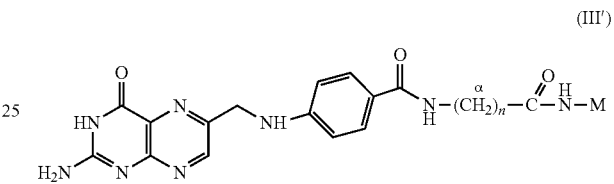

in which M and n are as defined above. Thus, n is an integer between 1 and 10. According to a preferred embodiment, n is an integer between 2 and 7, preferably between 3 and 5, advantageously n is the integer 3 or 5.

When Y' corresponds to a group of general formula (still), the conjugate according to the invention is represented by general formula (III"):

(III")

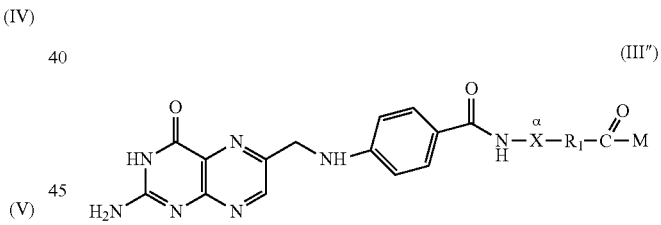

in which X, $R_1$, and M are as defined above.

According to a preferred embodiment, $R_1$ is —NH— and the conjugate according to the invention then responds to the following formula (III"):

(III")

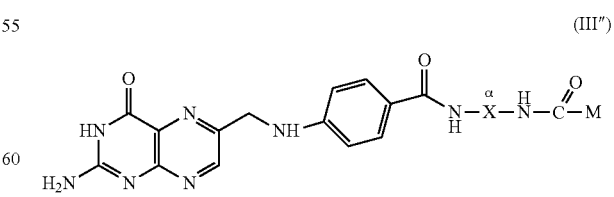

in which X and M are as defined above.

According to a particularly preferred embodiment, X is —$(CH_2)_n$— and the conjugate according to the invention responds to the following general formula (III"):

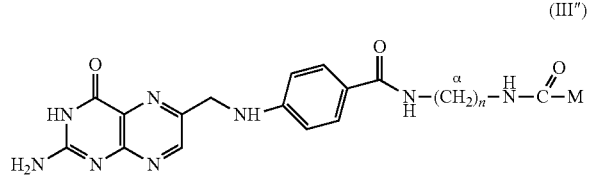

(III″)

in which M and n are as defined above. Thus n is an integer between 1 and 10. According to a preferred embodiment, n is an integer between 2 and 7, preferably between 3 and 5, advantageously n is the integer 3 or 5.

Another object of the invention relates to a process for in vitro assay of the folate(s) in a sample, such as a biological sample, said assay being a non-radioisotopic competition immunoassay, said process comprising the following steps:

a) bringing into contact, in said biological sample, (i) at least one binding partner of the folate(s), such as an antibody suitable to bind to the folate(s) or such as the folates receptor, with (ii) at least one compound selected from a folate derivative such as defined above and a conjugate according to the invention, at least one of said compounds (i) and (ii) being suitable to emit a signal, b) optionally leaving a sufficient time lapse to allow the competition reaction, c) measuring the intensity of the signal and deducing from it the folate(s) concentration present in said biological sample by reference to a calibration curve establishing a relationship between measured signal intensity and folate(s) concentration.

This assay process can be implemented in a biological sample of clinical origin, i.e. taken from a human or animal patient. In addition, this assay process also finds application in the assay of the folate(s) in a sample of agri-food origin, such as foods intended for human or animal consumption or food supplements. Generally, the assay process according to the invention is applicable whenever a folate(s) assay is required/necessary in a given sample.

Whatever the sample, of clinical origin or of food origin, the folates assay requires a prior step of treatment of the sample in order to dissociate the folates from other molecules present in these samples and with which they interact. Such dissociation techniques are well known to the man skilled in the art. By way of example, we can cite European patent EP 0382334 which discloses a method for preparation of serum samples for assay of vitamin B12 and folates. U.S. Pat. No. 4,418,151 discloses an alternative pre-treatment method. The manual of the Abbott Axsym Folate kit (Cat. No. B7K460, Abbott Laboratories) describes a protocol for preparation of a haemolysate from a whole blood sample in order to make all the folate molecules present in the red blood cells accessible to the assay.

The man skilled in the art, very well acquainted with non-radioisotopic competition immunoassay techniques will manage, without excessive difficulty, to implement steps b) and c). In particular he will be fully capable of constructing a calibration curve, on the basis of samples containing known concentrations of folate(s), thus establishing a relationship between the measured signal intensity and concentration of folate(s).

As mentioned above, competition immunological assay (also called "immunoassay by competition") is an assay widely known to the man skilled in the art. It consists in assaying the analyte, here the folate, in a sample in question, by creating competition between the analyte of the sample and a derivative of this analyte, here the folate derivative according to the invention, with regard to fixing to a binding partner of immunological origin (for example an antibody or an antibody fragment) or otherwise (for example the folates receptor). The binding of the derivative of the analyte in question and of the binding partner is revealed by means of the presence of a tracer.

The derivative of the analyte (in this case the folate derivative) can be used in the competition reaction, as indicated above, without prior bonding or after bonding to a marker to form a conjugate or tracer.

When the analyte derivative (in this case the folate derivative) is not bonded to a marker (in which case, it does not form the tracer but the capture partner), the binding partner is then labelled to form the tracer of the reaction. When the analyte derivative (in this case the folate derivative) is bonded to a marker (in this case a marker molecule Mm) to form a conjugate, the latter then constitutes the tracer and the binding partner then becomes the capture partner.

The measured signal, emitted by the tracer, is then inversely proportional to the quantity of folate(s) present in the sample to be assayed.

As binding partner of the folate(s), is used any molecule capable of binding to the folate(s). As examples of binding partner to the folate(s), can be cited antibodies, antibody fragments, nanofitins, the folates receptor or any other protein known to bond to the folate(s) with sufficient affinity to perform the non-radioisotopic competition immunoassay according to the invention.

When antibodies are used as binding partners, they can be, for example, polyclonal or monoclonal antibodies.

Polyclonal antibodies can be obtained by immunisation of an animal with the target folate as immunogen, followed by recovery of the required antibodies in purified form, by taking serum from said animal and separation of said antibodies from the other constituents of the serum, in particular by affinity chromatography on a column on which is fixed an antigen specifically recognised by the antibodies, in particular the immunogen.

Monoclonal antibodies can be obtained by the hybridomas technique widely known to the man skilled in the art. The monoclonal antibodies can also be recombinant antibodies obtained by genetic engineering, by techniques well-known to the man skilled in the art.

As examples of antibody fragments can be cited the Fab, Fab', F(ab')$_2$ fragments as well as the scFv (Single chain variable fragment), dsFv (Double-stranded variable fragment) chains. These functional fragments can in particular be obtained by genetic engineering.

Nanofitins (trade name) are small proteins which, like antibodies, are capable of binding to a biological target thus permitting its detection, its capture or quite simply its targeting in an organism.

The binding partners used can be specific or not specific to the folate(s). They are called specific when they are capable of binding exclusively or virtually exclusively to the folate(s). They are called non-specific when the binding selectivity to the folate(s) is low, and they are capable of binding to other ligands, such as proteins or antibodies.

According to a preferred embodiment, at least one specific binding partner is used in the context of the non-radioisotopic competition immunoassay process according to the present invention.

When they are used in capture, the binding partners or the folate derivatives according to the invention can be bound or not bound to a support by any technique known to the man skilled in the art.

The second step b) of the process of the invention is a conventional step of a competition immunoassay process.

The last step c) of the process according to the invention consists in determining the folate(s) concentration. The measured signal is inversely proportional to the quantity of folate(s) in the sample. In order to determine the folate(s) concentration, the intensity of the signal is measured and this intensity is plotted on a calibration curve previously obtained by techniques widely known to the man skilled in the art. Thus, for example, the calibration curve is obtained by performing a competition immunoassay using the same binding partner as well as increasing quantities of folate(s). A curve is thus obtained by placing, for example, the folate(s) concentration on the abscissa and the corresponding signal obtained after immunoassay on the ordonnate.

When compound (ii) is a conjugate according to the invention, as described above, which constitutes an embodiment of the invention, the signal is generated by the tagging labelling of the labelling molecule Mm, as described above.

When compound (ii) is a folate derivative of the invention, as described above, i.e. it is not bound to a marker molecule Mm, the signal consists in the direct reading of the binding partner/folate derivative binding, which can in particular be performed by plasmon surface resonance or by cyclic voltammetry.

Preferably, compound (ii) is a conjugate according to the invention.

As indicated above, the folate derivatives and conjugates according to the invention can be used to assay folate(s) in a sample. Preferably, these derivatives and conjugates are used to assay a plurality of (at least two) folates, i.e. a plurality of folate forms (in particular the reduced forms) in said sample.

According to a particular embodiment of the invention, the folate derivatives and conjugates mentioned above are used to assay the total folate in a sample.

The invention also relates to an in vitro diagnostic method intended to determine whether a human or animal patient, preferably human, has a folate(s) deficiency, said method comprising the following steps:

a) in a biological sample, preferably of whole blood, of plasma or of serum, taken from said patient, assaying the folate(s) by implementing the in vitro assay process according to the invention, in order to deduce from it the folate(s) concentration in the biological sample, b) comparing said concentration with a threshold value, corresponding to a predetermined folate(s) concentration below which a patient is considered as deficient in folate(s), and c) if the assayed concentration is less than said threshold value, deducing from this that the patient has a folate(s) deficiency.

Another object of the invention relates to a folate derivative of general formula (I)

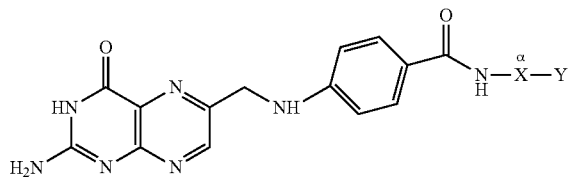

(I)

in which:

X is as defined above;

Y is a group of electrophilic centre type or of nucleophilic centre type, preferably a group of electrophilic centre type, suitable to allow the formation of an amide, ester, or thioester bond, preferably amide or ester, advantageously amide, between Y and a functional group carried by a separate molecule M; and in which:

when X is a linear and saturated hydrocarbon chain comprising a number of carbon atoms equal to 2, Y is not an $-(O-CH_2-CH_2)_2-NH_2$ group;

when Y is a group of nucleophilic centre type consisting in a primary amine, X comprises a number of carbon atoms different from 6, when Y is a group of electrophilic centre type, the latter respond to the following general formula (II):

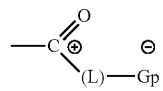

(II)

in which Gp is a leaving group, optionally connected to the carbonyl function by an L arm, Gp being suitable to be dissociated from the group of electrophilic centre type in a reaction with a nucleophilic group carried by said separate molecule M, such as a primary amine, and in which, when L is absent and Gp is —OH, X comprises a number of carbon atoms greater than 4.

According to a particular embodiment, the functional group Y does not comprise an $-(O-CH_2-CH_2)-$ structure.

This folate derivative of general formula (I) is suitable for implementation of a non-radioisotopic competition immunoassay of the folate(s) in a sample. It does not therefore include a radioisotope/radioelement.

Said folate derivative of general formula (I) as such is not labelled. Where necessary, said folate derivative will be labelled after bonding to a marker molecule Mm, said bonding comprising the formation of a covalent bond between the functional group Y of said folate derivative and a functional group carried by said marker molecule Mm.

The folate derivative of general formula (I) is different from the NSP-DMAE-HD-pteroate compound represented by formula (A) in claim 1.

According to a particular embodiment, Y is different from group (C):

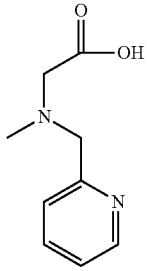
(C)

According to another particular embodiment, when X is a linear and saturated hydrocarbon chain comprising a number of carbon atoms equal to 2, Y is different from the following groups (D) and (E):

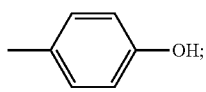
(D)

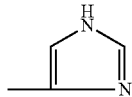
(E)

According to a modification of this "other particular embodiment", Y is different from the above-mentioned groups (D) and (E), and this whatever the definition of X.

Preferably, said reaction of the group of electrophilic centre type of general formula (II) with said nucleophilic group carried by said molecule M—such as a primary amine—is a nucleophilic substitution reaction.

According to a particular embodiment, when Y is a group of nucleophilic centre type, the latter consists in a functional group different from a primary amine.

According to a preferred embodiment, when Y is a group of electrophilic centre type responding to general formula (II), (L)-Gp is a group selected from: —OH, —NH—$(CH_2)_m$—COOH, —$N_3$,

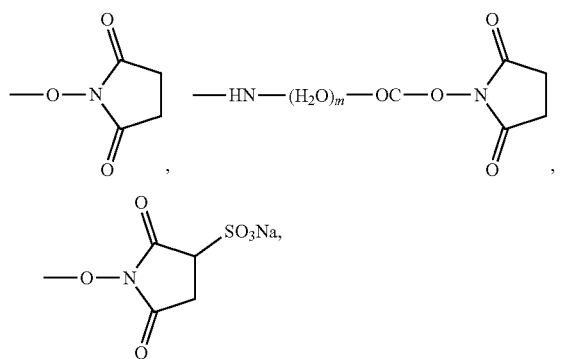

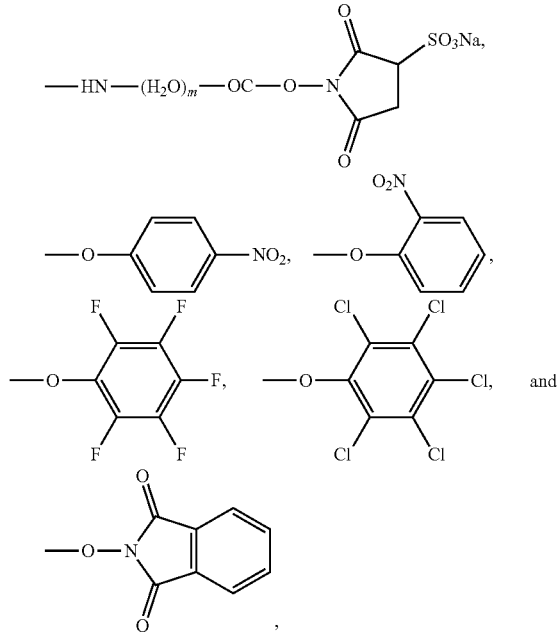

m being an integer of between 1 and 10, preferably between 1 and 5, advantageously between 1 and 3, in which when L is absent and Gp is —OH, X comprises a number of carbon atoms greater than 4.

Preferably, when Y is a group of electrophilic centre type of formula (II), (L)-Gp is selected from:
—OH and —NH—$(CH_2)_m$—COOH and,

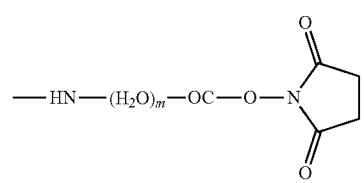

m being between 1 and 10 and preferably m being equal to 1,
in which when L is absent and Gp is —OH, X comprises a number of carbon atoms greater than 4.

According to a particularly advantageous embodiment, when Y is a group of electrophilic centre type of formula (II), (L)-Gp is:

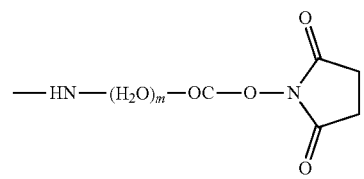

According to a particular embodiment, and still when Y is a group of electrophilic centre type of general formula (II), Gp is a group different from an —OH (hydroxyl group) group.

The invention also relates to a conjugate comprising a folate derivative according to the invention and a separate molecule M, said derivative and said molecule M being linked by at least one amide, ester, or thioester bond, preferably an amide or ester bond, advantageously an amide bond, between Y and a functional group carried by said molecule M.

According to a particularly preferred embodiment, said molecule M is selected from chemical arms or "linkers" or from the marker molecules $M_m$, said molecule M preferably being a marker molecule Mm permitting the direct or indirect labelling of said folate derivative (the latter then being called "tagged conjugate").

Another object of the invention relates to a kit permitting the implementation of the process according to the invention, said kit comprising:
(i) at least one binding partner of said folate(s), such as an antibody suitable to bind to the folate(s) or such as the folates receptor,
(ii) at least one compound selected from a folate derivative such as defined above and a conjugate according to the invention, at least one of said compounds (i) and (ii) being suitable to emit a signal, and
at least one calibration means.

Of course, this kit (also called "detection kit") can comprise other constituents allowing or favouring the implementation of the immunoassay according to the invention, such as, for example, wash buffers and one or more other reagent(s) allowing the labelling to be visualised, or the emission of a detectable signal.

The folate derivatives of the invention can be used in two different manners in the processes for assay of the folate(s) by competition immunoassay, such as diagnostic tests. Indeed, they are either used as such, or they are used bonded to another molecule to form a conjugate.

Said "other molecule" is either a direct or indirect marker, or a chemical arm or "linker", or a chemical compound the bonding of which to a folate derivative has an advantage, in particular for implementation of a folate assay by competition immunoassay (preferably non-radioisotopic).

Thus, the present invention also has as its object conjugates comprising or formed of a folate derivative such as described above and of another molecule, in particular of a marker or of a chemical arm.

By marker, is understood any molecule capable of directly or indirectly generating a detectable signal. A non-limiting list of these direct detection markers consists in:
enzymes which produce a detectable signal for example by colorimetry, fluorescence, luminescence, like horseradish peroxidase, alkaline phosphatase, β-galactosidase, glucose-6-phosphate dehydrogenase,
chromophores such as fluorescent, luminescent, colourant compounds,
fluorescent molecules such as Alexa or phycocyanins,
electrochemiluminescent salts such as organometallic derivatives based on acridinium all ruthenium.

Indirect detection systems can also be used, like for example ligands capable of reacting with an anti-ligand. The ligand then corresponds to the marker molecule Mm to constitute, with the folate derivative mentioned above, the conjugate of the invention.

The ligand/anti-ligand pairs are well known to the man skilled in the art. By way of example can in particular be cited the following pairs: biotin/streptavidin, hapten/antibody, antigen/antibody, peptide/antibody, sugar/lectin, polynucleotide/complementary polynucleotide.

The anti-ligand can then be directly detectable by the direct detection markers described above or itself be detectable by another ligand/anti-ligand pair, and so on.

These indirect detection systems can lead, under certain conditions, to amplification of the signal. This technique of amplification of the signal is well known to the man skilled in the art, and reference can in particular be made to prior patent applications FR98/10084 and WO-A-95/08000 of the Applicant.

Depending on the type of labelling used, the man skilled in the art will add reagents permitting the labelling to be visualised or the emission of a signal detectable by any appropriate type of measuring apparatus, like for example a spectrophotometer, a spectrofluorometer or a camera (for example a high-definition camera).

By chemical arm or "linker", is understood any molecule able to be bonded to the derivative according to the present invention, said molecule being in addition capable of fixing onto a solid phase, covalently or non-covalently, in selective or non-selective manner.

As indicated above, the folate derivatives and the corresponding conjugates according to the present invention are particularly useful for in vitro determination of the folate(s) concentration in a sample of clinical origin (for example a biological sample taken from a human or animal patient) or a sample of agri-food origin (taken from a food or from a food supplement).

The determination of the folate(s) concentration using the derivative or conjugate according to the present invention may be performed in the culture supernatant or in the cellular lysate.

Another object of the invention relates to the process for obtaining a derivative according to the invention, said process comprising the following steps:
a) synthesising, from pteroic acid, the compound of general formula (VI):

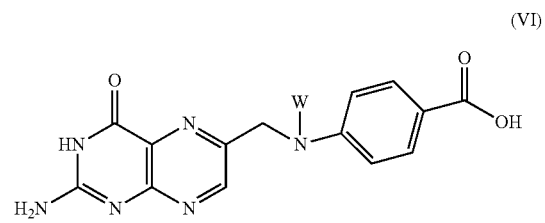

(VI)

in which W represents a group increasing the solubility of said compound in organic solvent(s), such as a trifluoroacetyl group (COCF3),
b) reacting said compound of formula (VI), obtained in step a), with a compound of following general formula (VII):

NH$_2$—X—Y"—Z (VII)

under conditions permitting the obtaining, by bonding, of the compound of following general formula (VIII):

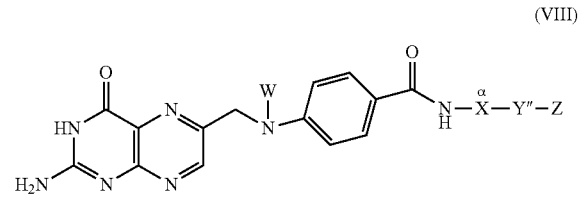

(VIII)

X being as defined above,
Z being an inert group, preferably alkyl or aryl, and

Y" being a derivative of the Y group (such as defined above) after bonding to said Z group.

c) unprotecting, under conditions permitting this unprotection, the compound of formula (VIII), in order to obtain the folate derivative of formula (I) according to the invention.

According to a preferred embodiment, in step b), said compound of formula (VI), obtained in step a), is reacted with a compound of following general formula (VII):

NH$_2$—X—Y"—Z    (VII)

in which Y" is —C(O)O—,
in order to prepare a folate derivative of formula (I), in which Y is —COOH.

In this preferred embodiment, if Z is a methyl or ethyl group, Y—Z is respectively —C(O)O—CH3 or —C(O)O—CH3 in compounds of formulae (VII) and (VIII). If Z is an aryl group, then Y—Z is —C(O)O—Ar in said compounds (Ar symbolising this aryl group).

At the end of the unprotection step c), and still within this preferred embodiment, the above-mentioned group —C(O)O— results in a —COOH group. The folate derivative of general formula (I) according to the invention thus obtained is called "acid" folate derivative. According to a preferred aspect of this embodiment, the process then comprises, after step c), the following additional step:

d) obtaining, from said acid folate derivative (in which Y=—COOH), the NHS-folate derivative ester, i.e. the compound responding to the following general formula (IX):

(IX)

in which X is as defined above.

This compound of general formula (IX) represents one of the preferred folate derivatives or the preferred folate derivative within the meaning of the present invention. Advantageously, X is a saturated linear aliphatic hydrocarbon chain comprising a number of carbon atoms between 1 and 10, preferably between 2 and 7, advantageously between 3 and 5.

The methods for obtaining NHS (N-hydroxysuccinimides) esters are well known to the person skilled in the art. Examples of obtaining folate derivatives of formula (IX) according to the invention are presented below (cf. examples 3 and 4 below) as illustrative and non-limiting examples.

Pteroic acid is a commercially available compound. Unfortunately, this compound proves to have low solubility in organic solvents. It is therefore transformed, in step a), into a compound of general formula (VI) to facilitate the continuation of the present process.

Preferably, this compound of formula (VI) is N-trifluoroacetylpteroic acid (W=—COCF3). In this case, the pteroic acid is made to react, preferably, with trifluoroacetic anhydride, advantageously protected by nitrogen.

As indicated above, step b) is performed under reaction conditions allowing the required reaction to be obtained. These reaction conditions, preferably, include the use of a bonding agent.

As indicated above, the inert group Z consists, for example, in a methyl or ethyl group (in particular when Y" is —C(O)O—, to give-C(O)O-Mp or —C(O)O-Et) or in an Fmoc group (in particular when Y" is —NH—, to give-NH-Fmoc).

According to a particular embodiment, step b) comprises the following two sub-steps:

b.1) forming, from the compound of formula (VI), obtained in step a), an active intermediate such as N-trifluoroacetylpteroic acid isobutylformiate of the following general formula (VI'):

(VI')

b. 2) reacting said active intermediate obtained in step b.1) with a compound of following general formula (VII):

NH$_2$—X—Y"—Z    (VII)

under conditions allowing the obtaining, by bonding, of the compound of following general formula (VIII):

(VIII)

in which W, X, Y" and Z are as defined above.

According to a preferred embodiment, in steps b) and/or b.2) mentioned above, the bonding is obtained by transamidification.

The unprotection step c) results in the elimination of the W group and, concurrently or subsequently, of the Z group, advantageously under the protection of nitrogen.

This unprotection step c) is, preferably, performed in a basic medium, for example in a solution of NaOH. This basic solution allows the elimination of the W group and, concurrently, of the Z group (consisting for example in a methyl or ethyl group), by saponification reaction.

DETAILED DESCRIPTION

Figure 1:
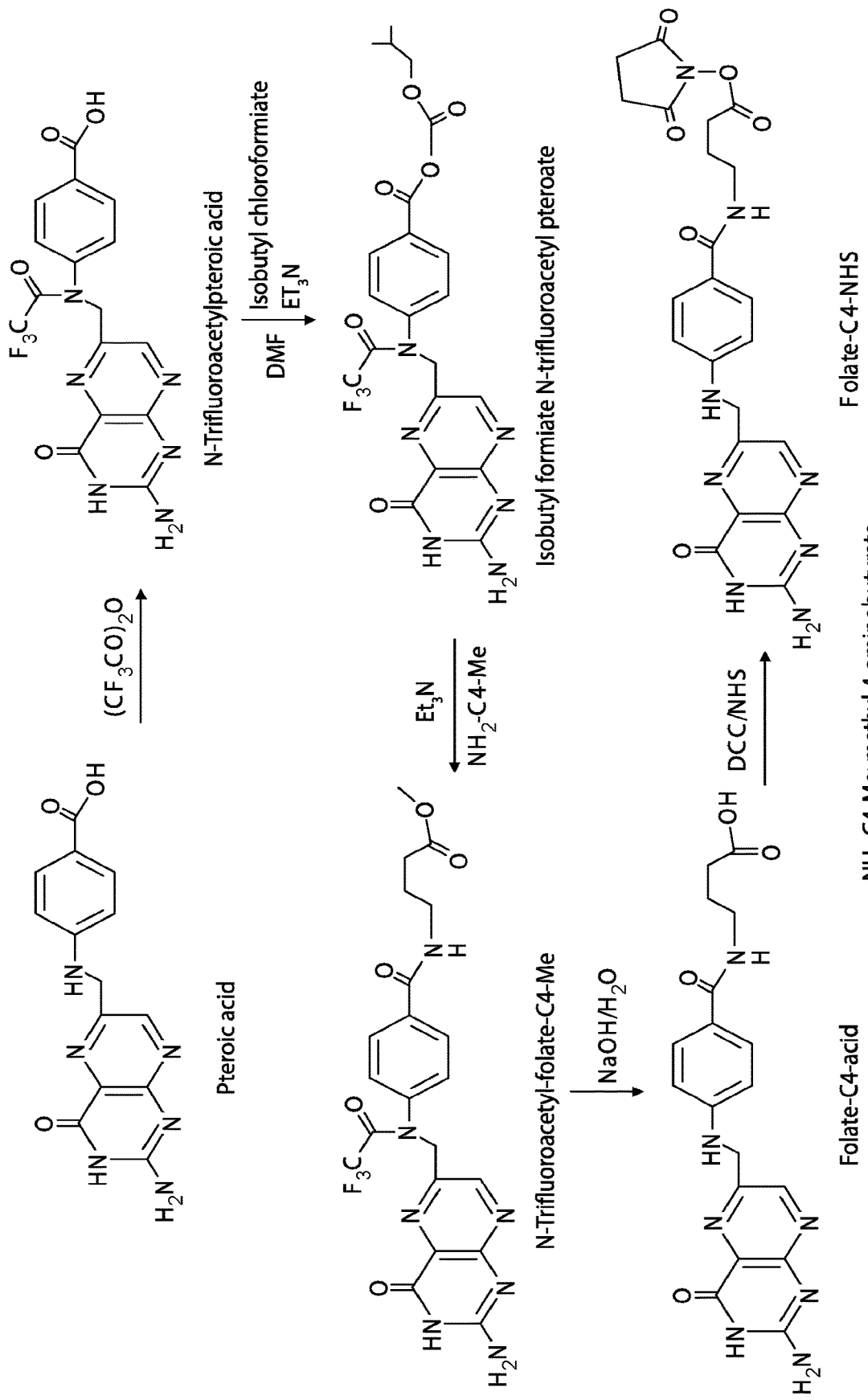

The invention will be better understood by means of the following examples which are given in illustrative and non-limiting manner, with reference to FIGS. 1 and 2, in which:

FIG. 1 shows the synthesis steps of folate-C4-acid (4-(4-((2-amino-4-oxo-3,4-dihydropteridin-6-yl)methylamino)benzamido)butanoic acid) and NHS—C4-folate, and FIG. 2 shows the synthesis steps of folate-C6-acid (6-(4-((2-amino-4-oxo-3,4-dihydropteridin-6-yl)methylamino)benzamido)hexanoic acid) and NHS—C6-folate.

EXAMPLE 1: PREPARATION OF 4-(4-((2-AMINO-4-OXO-3,4-DIHYDROPTERIDIN-6-YL)METHYLAMINO)BENZAMIDO) BUTANOIC ACID (FOLATE-C4-ACID)

For the sake of clarity, the compound called "folate-C4-acid" is a derivative according to the invention, responding to the following general formula (I):

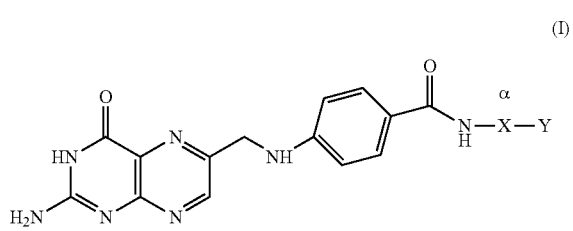

in which X is a linear and saturated aliphatic hydrocarbon chain comprising 3 carbon atoms and Y is a group of electrophilic centre type responding to general formula (II):

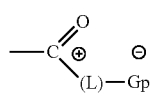

in which L is absent and Gp is —OH.

1.1. Introduction

The reagents pteroic acid (CAS-Nr. 119-24-4), trifluoroacetic anhydride (CAS-Nr. 407-25-0), methyl 4-aminobutyrate (CAS-Nr. 3251-07-8), isobutyl chloroformiate (CAS-Nr. 543-27-1) amino-6-hexanoic acid (CAS-Nr. 60-32-2 also called 6-aminocaproic acid) and anhydrous dichloromethane (CAS-Nr. 75-09-2) were obtained from Sigma-Aldrich.

At each synthesis step, high pressure liquid chromatography (HPLC) is used to monitor the reaction progress and for analysis of the products. The column used is a Vydac 218TP54, C18, 250×4.6 mm, 5 µm and the eluent is a gradient acetonitrile, water (0.1% trifluoroacetic acid) mixture.

1.2. Step 1: Obtaining N-Trifluoroacetylpteroic Acid 500 mg (1.60 mmole) of pteroic acid are introduced into a 50 mL flask provided with magnetic agitation, with an inlet and an outlet for protection nitrogen. 10 mL of trifluoroacetic anhydride are added under nitrogen protection, drop by drop, over 30 minutes. The reaction mixture is agitated at ambient temperature for 24 hours in the dark. The reaction medium is evaporated under reduced pressure at ambient temperature and the residue is dried under vacuum for 1 hour. The product obtained is washed with 5 mL of ethyl ether and then dried under vacuum. The product is analysed by HPLC and used directly for the continuation of the synthesis.

1.3. Step 2: Obtaining N-Trifluoroacetyl-Folate-C4-Me

A mixture of 171 mg (0.42 mmole) of N-trifluoroacetylpteroic acid, 0.111 mL of triethylamine (CAS-Nr. 121-44-8) and 2 mL of dry dimethylformamide (DMF, CAS-Nr. 68-12-2) is prepared and agitated at ambient temperature under nitrogen for 45 minutes to give medium No. 1. In another 10 mL flask, 150 mg (0.98 mmole) of methyl 4-aminobutyrate hydrochloride are mixed with 2 mL of dry DMF, and then 0.111 mL of triethylamine are added. After agitation for 30 seconds, the mixture obtained is added under nitrogen protection to the prepared medium No. 1. The agitation is maintained at ambient temperature for 3 hours and the reaction is monitored by HPLC. The reaction medium is dried, without heat under vacuum. The residue is purified by silica gel 60 chromatography (0.040-0.063 mm, Merck Cat. No. 109385) with dichloromethane/methanol eluent, 5/1, v/v. 85 mg of product are obtained, which corresponds to a 40% yield. The purity is 96%, determined by HPLC.

1.4. Step 3: Obtaining Folate-C4-Acid 85 mg (0.168 mmole) of prepared N-trifluoroacetyl-folate-C4-Me acid are mixed with 6 mL of methanol. 2 mL of a 1N NaOH mixture are added. The mixture is agitated at ambient temperature and in the dark for 16 hours. The reaction medium is neutralised at pH 2 with 50% of trifluoroacetic acid and then dried under reduced pressure at ambient temperature. The residue is washed with 10 mL of the demineralised water and dried under vacuum. 66 mg of folate-C4-acid are obtained, which corresponds to a yield of 98%. The purity is 97.2%, determined by HPLC.

The synthesis of folate-C4-acid is summarised in FIG. 1.

EXAMPLE 2: PREPARATION OF 6-(4-((2-AMINO-4-OXO-3,4-DIHYDROPTERIDIN-6-YL)METHYLAMINO)BENZAMIDO) HEXANOIC ACID (FOLATE-C6-ACID)

The folate derivative called "folate-C6-acid" is a derivative according to the present invention responding to the following general formula (I):

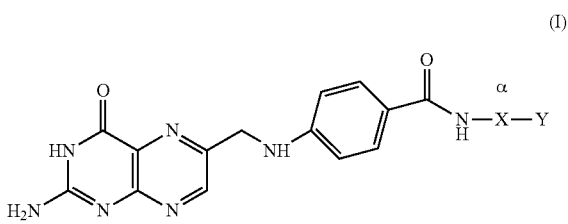

in which X is a linear and saturated aliphatic hydrocarbon chain comprising 5 carbon atoms, and in which Y is a group of electrophilic centre type, responding to the following general formula (II):

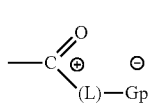

in which L is absent and Gp is —OH.

Folate-C6-acid (6-(4-((2-amino-4-oxo-3,4-dihydropteridin-6-yl)methyl-amino) benzamido) hexanoic acid) is synthesised in similar manner to folate-C4-acid. In the above-mentioned step 2, the methyl 4-aminobutyrate ($NH_2$—C4-

Me) arm is replaced by an ethyl 6-aminocaproate arm (NH$_2$—C6-Et, ethyl ester of amino-6-hexanoic acid). This compound is prepared from amino-6-hexanoic acid in the presence of ethanol and acetyl chloride.

60 mg of folate-C6-acid are obtained from 171 mg of N-trifluoroacetylpteroic acid, which corresponds to an overall yield of 34%. The purity is 96%, determined by HPLC.

The synthesis of folate-C6-acid is summarised in FIG. 2.

Generally, the length of the hydrocarbon chain X in the derivative of general formula (I) can be varied by using, in step 2, alkyl aminoalkanoate reagents of which the length of the hydrocarbon part of the alkanoate varies (4 carbon atoms to obtain the compound called "folate-C4-acid"; 6 carbon atoms to obtain the compound called "folate-C6-acid").

EXAMPLE 3: PREPARATION OF THE ESTERS OF FOLATE-C4-NHS

The reagents, N-hydroxysuccinimide (NHS, CAS-Nr. 6066-82-6), 1,3-dicyclohexylcarbodiimide (DCC, CAS-Nr. 538-75-0), dimethylsulphoxide (DMSO, CAS-Nr. 67-68-5) and tetrahydrofuran (CAS-Nr. 109-99-9) were obtained from Sigma-Aldrich. 66 mg (0.166 mmole) of folate-C4-acid obtained in example 1, 28.8 mg (or 1.5×0.166 mmole) of NHS and 4 mL of dry DMSO are introduced into a flask. 41.1 mg (or 1.2×0.166 mmole) of DCC are introduced after 2 minutes of agitation. The agitation is maintained at ambient temperature in the dark for 48 hours. HPLC is used to monitor the progress of the activation. 7 mg of NHS and/or 4 mg of DCC are added and the agitation is maintained for 72 additional hours.

The reaction mixture is filtered and the solution obtained is mixed with 5 mL of dry tetrahydrofuran, then 170 mL of dry dichloromethane are added. The mixture is centrifuged after 15 minutes without agitation to recover the precipitate which is then dried under reduced pressure, without heat and in the dark. 42 mg of folate-C4-NHS are obtained, which corresponds to a yield of 51%. The purity is 69%, determined by HPLC.

The obtaining of the folate-C4-NHS ester is represented in FIG. 1 (cf. last reaction step).

EXAMPLE 4: PREPARATION OF THE ESTERS OF FOLATE-C6-NHS

As for the folate-C4-NHS ester, the reagents used are the following: N-hydroxysuccinimide (NHS, CAS-Nr. 6066-82-6), 1,3-dicyclohexylcarbodiimide (DCC, CAS-Nr. 538-75-0), dimethylsulphoxide (DMSO, CAS-Nr. 67-68-5) and tetrahydrofuran (CAS-Nr. 109-99-9), and were obtained from Sigma-Aldrich.

60 mg (0.14 mmole) of folate-C6 acid obtained in example 2, a mixture of DMF (2.5 mL) and DMSO (3 mL) dry solvents and 17.7 mg (1.1×0.14 mmole) of NHS are introduced into a flask. 32 mg (1.1×0.14 of DCC are added after 2 minutes of agitation. The agitation is maintained at ambient temperature, in the dark, for 24 hours. HPLC is used to monitor the progress of the activation. 30 mg of NHS and 30 mg of DCC are added and the agitation is maintained for 96 additional hours.

The reaction medium is centrifuged for 3 minutes at 3000 rpm and the recovered liquid is mixed with 30 mL of the mixture of the solvents dichloromethane/petroleum ether (1/1) and then centrifuged again to obtain a yellow precipitate. The product is dried under reduced pressure, without heat and in the dark. 21 mg (29% yield) of folate-C6-NHS are obtained with an HPLC purity of 83.1%.

The synthesis of the folate-C6-NHS ester is summarised in FIG. 2 (cf. last reaction step).

EXAMPLE 5: PREPARATION OF THE FOLATE-C4-NHS-ALKALINE PHOSPHATASE AND FOLATE-C6-NHS-ALKALINE PHOSPHATASE CONJUGATES 0.5 mL of a 20 mg/mL solution of recombinant alkaline phosphatase (ALP) (Roche, Ref. 03-535-452) are dialysed in Spectra/Por® tubing (cut-off level 6000-8000 Da, Spectrum Laboratories, USA) against 500 mL of 100 mM pH 8.3 carbonate buffer, under magnetic agitation, for one night, at +2/8° C. At the dialysis outlet, the concentration of the protein is determined by reading the optical density at 280 nm and this concentration is adjusted to 4 mg/mL.

The activated folate-C4-NHS and folate-C6-NHS esters obtained in example 2 are again used in DMSO at concentrations of 0.39 mg/mL and 0.5 mg/mL respectively, taking into account the purity.

For bonding of type (1-5) (one mole of alkaline phosphatase-5 moles of folate ester), 1.125 mL of the ALP solution are mixed with 256 µL of the folate-C4-NHS ester solution on the one hand and 255 µL of the folate-C6-NHS ester solution on the other. The percentage of DMSO in the reaction medium is 18.5%. The mixtures are incubated for one night at +2/8° C., under agitation on a wheel, in brown bottles.

Then, the reaction is stopped by addition of 10 mM lysine diluted in water. The quantity of lysine added is equimolar with the quantity of ester used for bonding. Therefore 20.5 µL, of the lysine solution are added for each of the bondings. The mixtures are incubated for 20 minutes on a wheel, at +18/25° C.

After stopping the reaction, 1 mL of each of the conjugates are dialysed in Spectra/Por® tubing (cut-off level approximately 7000 Da) for 3 h at +18/25° C. against 500 mL of 50 mM Tris pH 7.4, 9 g/L NaCl, 0.9 g/L azide buffer, under magnetic agitation. After 3 hours the tubes are transferred into new baths again containing 500 mL of the same buffer. The dialysis is continued overnight at +2/8° C., under magnetic agitation.

At the dialysis outlet, 10× conservation buffer (500 mM Tris pH 7.4, 90 g/L NaCl, 50 mM MgCl$_2$, 1 mM ZnCl$_2$, 0.01% SDS, 9 g/L azide) is added to the volumes recovered from the tubes. The volume obtained is approximately 1 mL per conjugate. Following dialysis the conjugates are only semi-purified: the dialysis permits elimination of the free, unreacted folate but not the free alkaline phosphatase. The conjugates can be used in an immunoassay at this stage and this is what has has been done in example 6 below.

To eliminate the free ALP and thus obtain conjugates with improved purity, hydrophobic interaction chromatography was performed using a RESOURCE Phenyl column (Cat No. 17-1186-01, GE Healthcare Lifesciences) mounted on an ÄKTA chromatography system. The flow rate of the pump is set to 2 mL/min. The TA buffer is 50 mM Tris pH 7.4, 9 g/L NaCl, 5 mM MgCl$_2$, 0.1 mM ZnCl$_2$, 0.9 g/L azide, 1.6 M (NH$_4$)$_2$SO$_4$. The TB buffer is 50 mM Tris pH 7.4, 9 g/L NaCl, 5 mM MgCl$_2$, 0.1 mM ZnCl$_2$, 0.9 g/L azide. The RESOURCE Phenyl column is equilibrated with TA buffer. The conjugate to be purified is mixed volume for volume with the TB buffer. Then, 2 volumes are added of the 50 mM Tris pH 7.4, 9 g/L NaCl, 5 mM MgCl$_2$, 0.1 mM ZnCl$_2$, 0.9 g/L azide, 3.2 M (NH$_4$)$_2$SO$_4$ buffer. This step allows the conjugate to be in the TA buffer. The injection of the conjugate (628 µL for folate-C4-NHS-ALP and 560 µL for folate-C6-NHS-ALP, in a 5 mL loop) is followed by a 20 mL wash in TA buffer. Then a 0 to 57% gradient of TB is applied for 30 mL, then a wash in 57% of TB buffer for 20 mL. This step is followed by a second gradient of 57 to 100% of TB applied for 30 mL, then by a wash in TB buffer for 20 mL. The last step consists in a gradient of 0 to 100% in water for 20 mL, and then a wash in water for 20 mL. The progress of the chromatography is monitored by measuring the optical density at 280 nm. The fractions from 74 mL of elution up to 104 mL (or in total 30 mL) are recovered, combined and then concentrated by diafiltration using an Amicon cell (Amicon stirred cells, Millipore), an Amicon PM membrane with a cut-off level of 10 000 Da and the TB buffer. In this step, the volume of the conjugate solution is reduced to approximately 0.5 mL. The conjugates are stored at +2/8° C. until their use in an immunoassay.

EXAMPLE 6: VITAMIN B9 ASSAY USING THE CONJUGATES FOLATE-C4-NHS-ALKALINE PHOSPHATASE AND FOLATE-C6-NHS-ALKALINE PHOSPHATASE AND COMPARISON WITH THE AXSYM ASSAY CONJUGATE (ABBOTT LABORATORIES)

The immunological assays were performed using the VIDAS® automated immunoassay analysis system (bioMérieux). The single-use cone is used both as the solid phase for the reaction and as the pipetting system. The cartridge is composed of 10 wells covered with a sealed and labelled sheet of aluminium. The first well includes a previously cut-out part to facilitate the introduction of the sample. The last well is an optical cuvette in which the fluorescence of the substrate is measured. The different reagents necessary for the analysis are contained in the intermediate wells.

a) Sensitisation and Passivation of the Cones

The cones were sensitised with 300 μL of an "anti-folate binding protein" monoclonal mouse antibody (clone P8C5E4) diluted to 5 μg/mL in a 0.2 M tris, pH 6.2 buffer. After 6 hours of incubation at +18/25° C., a wash is performed with a 1M solution of NaCl. Then, 300 μL of a solution of "folate binding protein" (FBP, Cat. No. F0524, Scripps Laboratories) diluted to 6 ng/mL in a 100 mM, pH 7.4 NaCl 0.15 M phosphate buffer containing human albumin and a sugar are added. The sensitisation/passivation is continued at +18/25° C. overnight. The cones are emptied, dried and then stored at +4° C. until use.

b) Preparation of a Range from Biological Samples

Human serum samples containing different folate concentrations were obtained from the Biomnis laboratory (Lyon, France). The samples having the same concentrations were mixed in order to increase the available volume per range point. The mixtures were then aliquoted at 120 μL and frozen at −20° C. until use. The nominal concentrations of each of the points are: 1.3 ng/mL-4.4 ng/mL-10 ng/mL-20 ng/mL. The range point 0 ng/mL was prepared by dissolving 10% of human serum albumin in 10 mM pH 8.5, 0.15 M NaCl phosphate borate buffer.

c) Extraction of the Samples

The objective of the extraction step is to dissociate the serum folate from its binding partners and to make it accessible for the assay. To 250 μL of sample are added 50 μL of a 62.5 mg/mL TCEP (tris2-carboxyethyl)phosphine) solution and 215 μL of a solution of 0.8N NaOH+0.005% KCN. The mixture is incubated at +18/25° C. for 15 minutes, in the dark. After this stage, 1 mL of 1M pH4 glycine buffer is added.

d) Modus Operandi of the Immunoassay Reaction

The sample to be assayed (200 μL), extracted according to the protocol described in c), is introduced into the first well of the cartridge. Then all the assay reaction steps are performed automatically by the VIDAS®. The cones prepared according to the protocol described in a) are wetted by a 1M pH 10, 0.1 M NaCl glycine and 2% saccharose buffer. The sample to be assayed is mixed with 200 μL of a dilution of conjugate which is a folate derivative labelled with alkaline phosphatase. The sample/conjugate mixture is incubated in the cone for approximately 20 minutes during which competition takes place between the folates present in the sample and the folate derivative of the conjugate for FBP protein sites presented on the cone. Then, 3 successive washes with a 100 mM Tris pH 7.4, 0.15M NaCl, 0.1% Tween® 20 buffer are performed in order to eliminate the non-fixed compounds. At the final revelation step, the 4-methylombelliferyl phosphate substrate is aspirated and then discharged into the cone; the enzyme of the conjugate catalyses the hydrolysis reaction of this substrate into 4-methylombelliferone, the emitted fluorescence of which is measured at 450 nm. The value of the fluorescence signal is inversely proportional to the folate concentration present in the sample.

In the experiment presented in Table 1, three conjugates have been compared. These are the two conjugates obtained in example 3 and, as reference, the conjugates used in the Abbot Axsym Folate kit (Cat. No. B7K460, Abbot Laboratories).
  (i) the folate-C4-ALP and folate-C6-ALP conjugates were diluted to a concentration of between 0.50-0.75 ng/mL in the conjugate diluting buffer which contains 100 mM of Tris pH 8.5, 0.15 M NaCl, 20 mg/L of mouse IgG, stabilisation agents, preserving agents and other additives.
  (ii) the conjugate of the folate Axsym kit is a conjugate of pteroic acid (folate analogue) and alkaline phosphatase. This conjugate was diluted to 1/80 with the conjugate diluting buffer before use in the VIDAS®.

The range points prepared in b) were measured with each assay format. Table 1 below summarises the results obtained with the RFV (=relative fluorescence value) signal and B/B0% ratio. The B/B0% ratio is the signal obtained for the range point tested divided by the signal obtained for the range point 0 ng/mL of folate, multiplied by 100.

TABLE 1

| [c] folate (ng/mL) | REF = Axsym conjugate | | Folate-C4-ALP | | Folate-C6-ALP | |
|---|---|---|---|---|---|---|
| | Signal (RFV) | B/B0% | Signal (RFV) | B/B0% | Signal (RFV) | B/B0% |
| 0 | 3399 | 100 | 3544 | 100 | 4118 | 100 |
| 1.3 | 3329 | 98 | 3095 | 87 | 3563 | 87 |
| 4.4 | 2442 | 72 | 2016 | 57 | 2619 | 64 |
| 10 | 925 | 27 | 995 | 28 | 1131 | 27 |
| 20 | 39 | 1 | 24 | 1 | 34 | 1 |

An 87% reduction in the signal is observed at 1.3 ng/mL of folate with the folate-C4-ALP and folate-C6-ALP conjugates of the invention, while with the reference conjugate the signal reduction scarcely begins.

Consequently, the assays using the folate-C4-ALP and folate-C6-ALP conjugates are more sensitive than the assay using the reference conjugate and permit better detection and quantification of concentrations less than 4.4 ng/mL, and even less than 1.3 ng/mL.

Regarding the folate derivatives and conjugates according to the invention, in particular those responding to general formulae (I), (I'), (III), (III'), (III"), (VI), (VI'), (VIII) and (IX) mentioned above, it should be noted that, even if the pterin part of these is shown diagrammatically in its ketone form, the present invention quite obviously covers all—and each of the—tautomeric forms of said folate derivatives and conjugates able to be obtained at said pterin part, and in particular the 2-amino-4-hydroxy-6-methylpteridin form.

BIBLIOGRAPHICAL REFERENCES

1. Antony A C, The biological chemistry of folate receptors, Department of Medicine, Indiana University School of Medicine, Indianapolis, Blood. 1992 Jun. 1; 79(11):2807-20
2. Reif V D, Reamer J T, Grady L T., Chromatic assays for folic acid, J Pharm Sci. 1977 August:66(8):1112-6 PMID: 894496
3. Dueker S R, Lin Y, Jones A D, Mercer R, Fabbro E, Miller J W, Green R, Clifford A J., Determination of blood folate using acid extraction and internally standardized gas chromatography-mass spectrometry detection, Anal Biochem. 2000 Aug. 1; 283(2):266-75 PMID:10906248
4. Pfeiffer C M, Fazili Z, McCoy L, Zhang M, Gunter E W, Determination of folate vitamers in human serum by stable-isotope-dilution tandem mass spectrometry and comparison with radioassay and microbiologic assay, Clin Chem. 2004 February; 50(2):423-32. Epub 2003 Dec. 11 PMID:14670827
5. Waxman S. and Schreiber C., Determination of folate by use of radioactive folate and binding proteins, Methods Enzymol. 1980; 66:468-83. No abstract available. PMID: 7374487
6. Hansen, S. I. and Holm, J., A competitive enzyme-linked ligand sorbent assay (ELLSA) for quantitation of folates, Anal Biochem. 1988 July; 172(1):160-4. PMID:3189760
7. Owen, W. E. and Roberts, W. L., Comparison of five automated serum and whole blood folate assays, Am J Clin Pathol. 2003 July; 120(1):121-6. PMID:12866382
8. Arcot J. and Shrestha A., Folate: methods of analysis, Food Science and Technology, School of Chemical Engineering and Industrial Chemistry, The University of New South Wales, Sydney, Australia, 2005

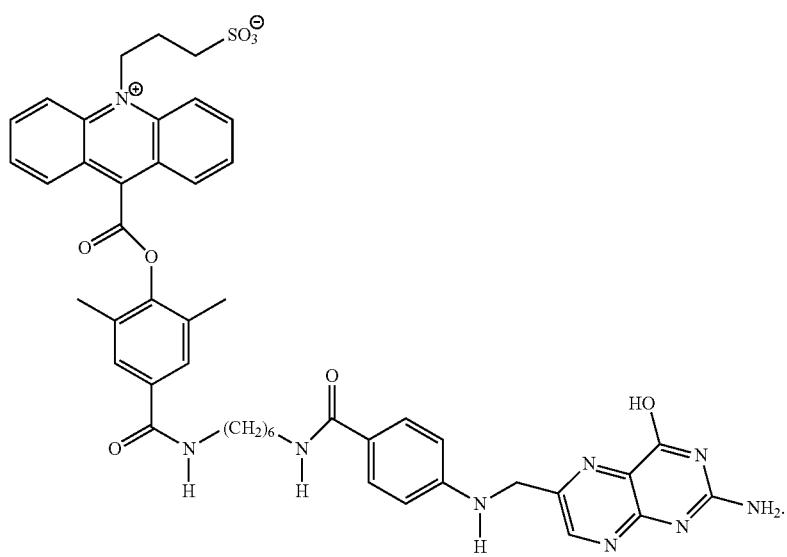

The invention claimed is:

1. A folate conjugate of general formula (III):

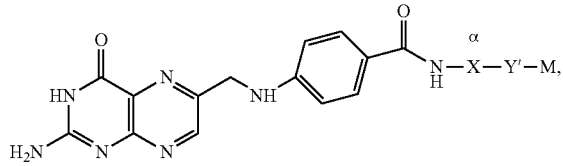
(III)

wherein
X is a linear aliphatic saturated hydrocarbon chain containing from 2 to 10 carbon atoms;
Y' is one of the following general formula (IV) or (V):

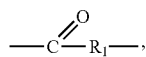
(IV)

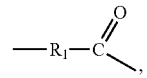
(V)

wherein $R_1$ is —NH—, —O—, or —S—;
M is a marker molecule capable of directly or indirectly generating a detectable signal;
and wherein the conjugate is not a compound of formula (A):

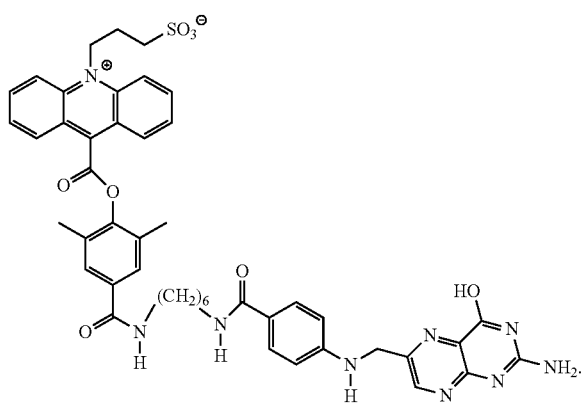
(A)

2. The conjugate according to claim 1, wherein X is a linear aliphatic saturated hydrocarbon chain containing from 2 to 7 carbon atoms.
3. The conjugate according to claim 2, wherein the hydrocarbon chain contains from 3 to 5 carbon atoms.
4. The conjugate of claim 1 wherein Y' is of general formula (IV).
5. The conjugate of claim 1 wherein $R_1$ is NH or O.
6. The conjugate of claim 1 wherein $R_1$ is NH.
7. The conjugate of claim 1, said conjugate being selected from the group consisting of

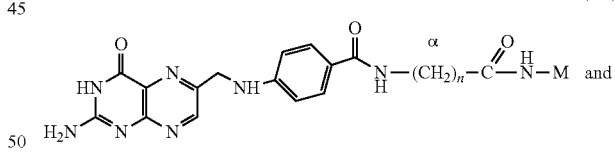
(III')

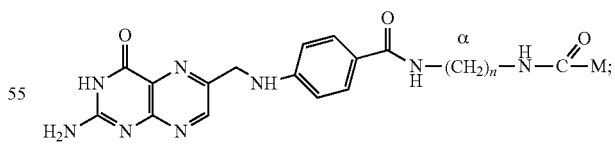
(III")

wherein n is an integer between 2 and 10.
8. The conjugate of claim 1 wherein M is selected from an enzyme, a chromophore, a fluorescent molecule or an electrochemiluminescent salt.
9. The conjugate of claim 8 wherein M is selected from the group consisting of horseradish peroxidase, alkaline phosphatase, β-galactosidase, glucose-6-phosphate dehydrogenase, Alexa, phycocyanins, and organometallic derivatives based on acridinium and ruthenium.

10. A kit comprising:
(i) at least one binding partner of folate(s) suitable to bind to the folate(s) or a receptor thereof;
(ii) at least one folate conjugate corresponding to general formula (III):

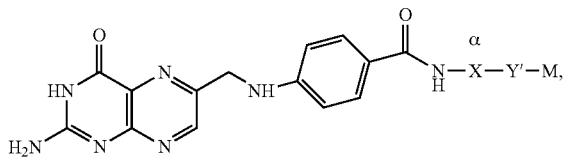

(III)

wherein
X is a linear aliphatic saturated hydrocarbon chain containing from 2 to 10 carbon atoms;
Y' is one of the following general formula (IV) or (V):

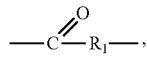

(IV)

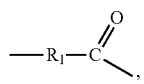

(V)

wherein $R_1$ is —NH—, —O—, or —S—;
M is a marker molecule capable of directly or indirectly generating a detectable signal;
and wherein the conjugate is not a compound of formula (A):

11. The kit according to claim 10, wherein X is a linear aliphatic saturated hydrocarbon chain containing from 2 to 7 carbon atoms.

12. The kit according to claim 11, wherein the hydrocarbon chain contains from 3 to 5 carbon atoms.

13. The kit of claim 10 wherein Y' is of general formula (IV).

14. The kit of claim 10 wherein $R_1$ is —NH— or —O—.

15. The kit of claim 10 wherein $R_1$ is —NH—.

16. The kit of claim 10, wherein the compound of formula (III) is selected from the group consisting of

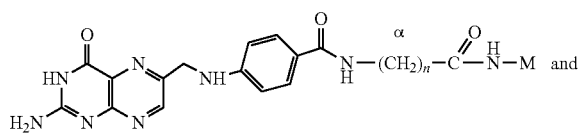

(III')

and

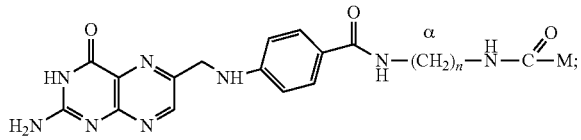

(III'')

wherein n is an integer between 2 and 10.

17. The kit of claim 10 wherein M is selected from an enzyme, a chromophore, a fluorescent molecule or an electrochemiluminescent salt.

18. The kit of claim 17 wherein M is selected from the group consisting of horseradish peroxidase, alkaline phosphatase, β-galactosidase, glucose-6-phosphate dehydrogenase, Alexa, phycocyanins, and organometallic derivatives based on acridinium and ruthenium.

* * * * *

(A)